United States Patent [19]

Gerber

[11] Patent Number: 5,750,132

[45] Date of Patent: May 12, 1998

[54] TREATMENT OF ADVERSE EFFECTS ASSOCIATED WITH ADMINISTRATION OF EXTRACELLULAR HEMOGLOBIN

[75] Inventor: Michael J. Gerber, Denver, Colo.

[73] Assignee: Somatogen, Inc., Boulder, Colo.

[21] Appl. No.: 451,370

[22] Filed: May 26, 1995

Related U.S. Application Data

[62] Division of Ser. No. 106,138, Aug. 13, 1993.

[51] Int. Cl.$^6$ .............. A61F 2/02; A61L 9/04; A61K 9/70; A61K 31/555

[52] U.S. Cl. .............. 424/423; 424/45; 424/434; 424/435; 424/449; 424/451; 424/464; 514/185; 514/815; 540/145

[58] Field of Search .............. 424/45, 423, 434, 424/435, 449, 451, 464; 514/185, 815; 540/145

[56] References Cited

U.S. PATENT DOCUMENTS

| | | | |
|---|---|---|---|
| 4,292,302 | 9/1981 | Keith et al. | 514/646 |
| 4,412,986 | 11/1983 | Kawata et al. | 514/356 |
| 4,529,719 | 7/1985 | Tye | 514/6 |
| 4,826,811 | 5/1989 | Sehgal, et al. | 514/6 |
| 5,028,588 | 7/1991 | Hoffman et al. | 514/6 |
| 5,173,426 | 12/1992 | Fischer et al. | 435/252.3 |
| 5,428,007 | 6/1995 | Fischer et al. | 514/6 |
| 5,478,806 | 12/1995 | Nho | 514/6 |
| 5,545,727 | 8/1996 | Hoffman et al. | 536/234 |

FOREIGN PATENT DOCUMENTS

| | | |
|---|---|---|
| 9013309 | 11/1990 | WIPO. |
| 9220368 | 11/1992 | WIPO. |
| 9220369 | 11/1992 | WIPO. |
| 9506657 | 2/1995 | WIPO. |

OTHER PUBLICATIONS

Mogattash et al, "Hemopoietic recovery from AZT toxicity with recombinant hemoglobin in a murine model of AIDS", Acta Haematol, (1994) 92(4) pp. 182–186.

Physicians Desk Reference (1993), Published by Medical Economics Data, Montvale, NJ/Terbutaline–PG 1057, 1060, 1059, 1364, 1365/Nifedipine–PG 1631, 1838, 1840, 1852, 1850/Nicardipine–PG 2393, 2395/Nitroglycerine–PG 958, 1191, 1353, 1387, 1388, 1800,1801, 1920, 2160, 2237, 2268, 2386/Atropine–PG 557, 608, 625, 719, 859, 1940, 1941, 2510, 2264/Na–Nitroprusside–PG 1999/Diphenhydramine–PG 1416, 1420, 1745, 1746, 1829/Cimetidine–PG 2321, /Methylpredinsolone–PG 2246, 2478./Hydrocortisone–PG 1532.2476./Glycogen–PG 1297./Naloxone–PG 952, 2169.

Snyder, S.R. & Walder, J.A./Chemically Modified And Recombinant Hemoglobin Blood Substitutes/Biotechnology Of Blood/(1991) Chapter 5: 101–116/ED. Goldstein/Butterworth–Heinemann.

Feola, M. Et Al/Clinical Trial Of A Hemoglobin Based Blood Substitute In Patients With Sickle Cell Anemia/Surg. Gyn. & Obstet./(1992) 174(5): 379–386.

Primary Examiner—Carolos A. Azpuru
Attorney, Agent, or Firm—Marianne F. Novelli; Theresa A. Brown; Ramsey R. Stewart

[57] ABSTRACT

The present invention relates to methods of lessening the severity and frequency of adverse effects associated with administration of extracellular hemoglobin comprising administration of a smooth muscle relaxant. Preferred smooth muscle relaxants are terbutaline and nifedipine, which can be administered in a prophylactic treatment, responsive regimented treatment or responsive intermittent treatment.

14 Claims, No Drawings

TREATMENT OF ADVERSE EFFECTS ASSOCIATED WITH ADMINISTRATION OF EXTRACELLULAR HEMOGLOBIN

This is a divisional of copending application Ser. No. 08/106,138 filed on Aug. 13, 1993.

This invention relates to methods of lessening the severity and frequency of adverse effects associated with administration of extracellular hemoglobin comprising administration of a smooth muscle relaxant.

BACKGROUND

When patients lose blood, it is usually necessary to replace the entire fluid volume lost. However, it is not usually necessary to replace all of the lost hemoglobin. The primary goal of hemoglobin replacement therapy is to transport oxygen from the lungs to peripheral tissues. Hemoglobin administration also increases and maintains plasma volume and decreases blood viscosity. While many volume expanding colloid and crystalloid solutions are now marketed, none can transport oxygen. The only current therapy with this capability is human blood transfusion.

In clinical practice, patients suffering acute loss of small to moderate amounts of blood require only volume resuscitation. More severe blood loss requires both volume replacement and replacement of oxygen carrying capacity. Only in situations such as massive blood loss, is it necessary to replace other blood components, such as platelets and clotting factors.

The following risks and limitations are currently associated with human blood transfusions:

1) Risk of infectious disease transmission (i.e., human immunodeficiency virus (HIV), non-A and non-B hepatitis, hepatitis B, *Yersinia enterolitica*, cytomegalovirus, Human T-cell Leukemia Virus 1).

2) Immunologic risks (i.e., mild hemolytic or fatal transfusion reaction, immunosuppresion, graft versus host reaction).

3) Need for typing and cross-matching prior to administration.

4) Availability of volunteer human donors.

5) Limited stability (unfrozen shelf life 42 days or less).

A number of extracellular hemoglobins have been proposed for use as oxygen delivery vehicles and other uses. However, all extracellular hemoglobins tested in animals or humans to date have some, albeit often mild or insignificant, side effects. The lessening or alleviation of such side effects or adverse effects is always a desirable goal of those administering any therapeutic agent.

Recombinant human hemoglobin (rHb1.1) is a novel hemoglobin-based oxygen carrier (HBOC) whose safety and efficacy will ultimately be studied in patients who have lost blood. To date, the safety and pharmacokinetics of rHb1.1 has been assessed in normal adult males.

Because rHb1.1 is a genetically-engineered, red blood cell-free HBOC, derived from fermentation rather than from whole blood, it may eliminate or minimize the risks and limitations associated with blood transfusions. The fact that rHb1.1 has volume replacement characteristics and oxygen transport properties, makes it a potential versatile replacement fluid for patients who have lost blood. It may also have usefulness in other clinical areas such as radiation or chemotherapy, erythropoiesis and anemia, coronary angioplasty, and treatment of sickle cell anemia or tissue ischemia. It may also have usefulness in other clinical areas.

Because administered rHb1.1 will circulate as a soluble plasma protein, it has the potential to maintain and expand intravascular volume by exerting colloid osmotic pressure effects. That portion of the osmotic pressure exerted by macromolecules, such as proteins, is the colloid osmotic pressure or oncotic pressure. The oncotic pressure of the intravascular plasma is higher an the oncotic pressure of the interstitial fluid. Plasma oncotic pressure is a key force in keeping water in the intravascular space, and thus maintaining intravascular volume. It counter balances the hydrostatic pressure within the microvasculature which tends to push water out of the intravascular space.

Oncotic pressure is proportional to the molar concentration of capillary-impermeable macromolecules. Normally, plasma albumin is responsible for 70–80% of the plasma oncotic pressure. The colloid osmotic pressure of rHb1.1 is similar to that of 5% human serum albumin when measured on a Wescor 4420 Colloid Osmometer. Since the molecular weight of albumin is 66,500 daltons and the molecular weight of rHb1.1 is 64,600 daltons, they will have a similar molarities and thus, similar oncotic pressure. Albumin is commonly formulated in 25 g doses. Therefore, the administration of 25 g of rHb1.1 would be expected to have volume expansion characteristics similar to the admistration of 25 g of albumin.

In addition to having important oncotic effects, rHb1.1 also has the capacity to transport oxygen. The oxygen equilibrium curve for rHb1.1 is similar to that of whole blood suggesting that rHb1.1 will load oxygen in the lungs and unload oxygen in the tissues in a manner similar to red blood cells. Administration of rHb1.1 will replace a portion of the oxygen transport capacity lost during hemorrhage, without exposing the patient to the risks of a blood transfusion.

SUMMARY OF THE INVENTION

The present invention relates to methods of lessening the severity and frequency of adverse effects associated with administration of extracellular hemoglobin comprising administration of a smooth muscle relaxant.

In one embodiment of the present invention, treatment of the adverse effects associated with administration of extracellular hemoglobin is by a method of prophylactically treating a patient or subject who is to receive an extracellular hemoglobin with a smooth muscle relaxant, preferably a β-adrenergic agonist or calcium channel blocker, more preferably terbutaline or nifedipine, most preferably terbutaline.

In another embodiment of the present invention, treatment of the adverse effects associated with administration of extracellular hemoglobin is by a method of responsive regimented treatment of a patient or subject with a smooth muscle relaxant, preferably nifedipine.

In another embodiment of the present invention, treatment of the adverse effects associated with administration of extracellular hemoglobin is by a method of responsive intermittent treatment of a patient or subject with a smooth muscle relaxant, preferably nifedipine.

Another aspect of the present invention is to novel methods of using extracellular hemoglobin as a treatment for various disorders selected from or resulting from the group consisting of radiation or chemotherapy, erythropoiesis and anemia, coronary angioplasty, and treatment of sickle cell anemia or tissue ischemia.

DETAILED DESCRIPTION OF THE INVENTION

The present invention relates to methods of lessening the severity (also referred to as intensity or degree) and frequency of adverse effects associated with administration of extracellular hemoglobin. The adverse effects that are the subject of this invention are those relating to gastrointestinal (GI) discomfort. The methods for alleviating the adverse effects include both prohylactic and responsive treatment of such adverse effects. Prophylactic treatment means administration of some pharmacological agents to treat the symptoms of the adverse effect prior to the onset of symptoms of adverse effect, preferably prior to commencement of administration of the extracellular hemoglobin. Preferably, prophylactic treatment also additionally includes repeated subsequent dosing of a pharmacological agents to treat the symptoms of the adverse effect after the commencement of administration of the extracellular hemoglobin. Responsive treatment means administration of some pharmacological agents only after onset or occurrence of symptoms of the adverse effect. Responsive treatment can be either intermittent or regimented.

Lessening the severity of the adverse effect means that the intensity of the adverse effect symptoms significantly decreases or the number of adverse effect symptoms included in a symptom complex significantly decreases. Lessening the frequency of the adverse effect means that the number of subjects or patients experiencing the adverse effect in a patient population significantly decreases. A significant decrease in either the intensity or number of adverse effect symptoms means the intensity or number of adverse effect symptoms at a given dose of extracellular hemoglobin is quantitatively decreased or it allows an increase in the dose of extracellular hemoglobin without quantitatively increasing the intensity or number of adverse effect symptoms. A significant decrease in the number of subjects or patients experiencing the adverse effect means a statistically significant fewer number of subjects or patients, larger than the error bar for the method of measurement, experience the adverse effect at the same intensity after intervention with treatment pharmacological agents. Such criteria apply even when subjects or patients in a given study at a given dose of extracellular hemoglobin experience no symptoms at all.

SOURCES AND ADMINISTRATION OF EXTRACELLULAR HEMOGLOBIN

For the purpose of the appended claims, an "extracellular hemoglobin" means a "hemoglobin" or "hemoglobin-like protein" comprises one or more heterotetramers composed of (a) two alpha globin-like and two beta globin-like polypeptides, (b) one di-alpha globin-like and two beta globin-like polypeptides, (c) two alpha globin-like and one di-beta globin-like polypeptides, (d) one di-alpha globin-like and one di-beta globin-like polypeptides, (e) one fused alpha/beta globin-like polypeptide and separate alpha and beta globin-like polypeptides, or (f) two fused alpha/beta globin-like polypeptides. A polypeptide of one tetramer maybe crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers. Preferably, the hemoglobin has the ability to bind oxygen with one or more heme prosthetic groups.

A human alpha globin-like domain or polypeptide is native human alpha globin or a mutant thereof differing from the native sequence by one or more substitutions, deletions or insertions, while remaining substantially homologous (as hereafter defined) with human alpha globin, and still capable of associating with beta globin. A beta globin-like domain or polypeptide is analogously defined. Subunits of animal hemoglobins or mutants thereof which are sufficiently homologous with human alpha or beta globin are embraced by the term "human alpha or beta globin-like domain or polypeptide." For example, the subunits of bovine hemoglobin are within the scope of these terms. The alpha- and beta-globin-like polypeptides may be referred to collectively as "globins". For the sake of convenience the term "polypeptide" may refer to a unitary chain or to a domain of a longer polypeptide chain. Preferably, the globin-like domain or polypeptide has the ability to incorporate heme.

A "genetically fused hemoglobin" is a hemoglobin-like protein comprising at least one "genetically fused globin-like polypeptide" (globin pseudooligomer), the latter comprising two or more globin-like domains which may be the same or different A di-alpha globin-like polypeptide is one which consists essentially of two alpha-globin-like polypeptide sequences (domains) connected by peptide bonds between the normal C-terminus of the first alpha-globin-like polypeptide (domain) and the normal N-terminus of the second alpha-globin-like polypeptide (domain). These two sequences may be directly connected, or connected through a peptide linker of one or more amino adds; the term "peptide bonds" is intended to embrace both possibilities. The di-alpha globin-like polypeptide preferably is capable of folding together with beta globin and incorporating heme to form functional hemoglobin-like protein. The di-beta globin-like polypeptide is analogously defined. A di-alpha or di-beta globin-like polypeptide with a mutation in only one of the component domains is called "asymmetric".

It is also possible to provide an "alpha/beta-globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

Even though the di-alpha hemoglobin does not dissociate into dimers, it is still cleared from the bloodstream, albeit more slowly than is the case for normal hemoglobin.

In determining whether a polypeptide is substantially homologous to alpha (or beta) globin, sequence similarity is an important but not exclusive criterion. Sequence similarity may be determined by conventional algorithms, which typically may allow introduction of a small number of gaps in order to achieve the best fit. Preferably, the alpha-globin-like polypeptides (or domains thereof) of the present invention have at least about 75% sequence identity with wild-type human alpha globin. However, a polypeptide of lesser sequence identity may still be considered "substantially homologous" with alpha globin if it has a greater sequence identity than would be expected from chance and also has the characteristic higher structure of alpha globin and similar biological activity. By way of comparison, Artemia's heme-binding domains are considered homologous with myoglobin even though the primary sequence similarity is no more than 27%, as alignment of the heme-binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

Well over a hundred mutants of human hemoglobin are known, affecting both the alpha and beta chains, and the effect of many of these mutations on oxygen-binding and other characteristics of hemoglobin are known. The human alpha and beta globins themselves differ at 84 positions. In addition, interspecies variations in globin sequence have been extensively studied. Dickerson, *Hemoglobin Structure, Function, Evolution and Pathology* ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin-like protein, which preferably will reversibly bind oxygen. The following resources may be used to identify conservative substitutions (and deletions or insertions):

(a) data on hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other substantially homologous proteins, and molecular modeling software for predicting the effect of sequence changes on such structures; and (f) data on the frequencies of amino acid changes between members of families of homologous proteins (not limited to the globin family). See, e.g., Table 1-2 of Schulz and Schirmer, *Principles of Protein Structure* (Springer-Verlag: 1979) and FIGS. 3–9 of Creighton, *Proteins Structure and Molecular Properties* (W. H. Freeman: 1983).

While the data from (a)–(d) is most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative I. small aliphatic, nonpolar or slightly polar residues— Ala, Ser, Thr (Pro, Gly)

II. negatively charged residues and their amides—Asn Asp Glu Gln

III. positively charged residues—His Arg Lys

IV. large aliphatic nonpolar residues—Met Leu Ile Val (Cys)

V. large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schirmer would merge I and II above. Note also that Tyr, because of its hydrogen bonding potential, has some kinship with Ser, Thr, etc.

In general, functionality (i.e., oxygen binding capability), which is preferred but not required, is less likely to be affected by mutations at surface residues, at least those not involved in either the heme crevice or the subunit contacts. In addition, "loops" connecting alpha helices, especially the D loop of the alpha helix, as well as free amino or carboxy termini, are more tolerant of deletions and insertions.

Hemoglobin is readily available from a number of sources. Slaughter houses produce very large quantities of hemoglobin in the form of blood which is currently usually sold as an inexpensive fertilizer. If particular species or breed of animal produces a hemoglobin especially suitable for a particular use, those creatures may be specifically bred for this purpose, in order to supply the needed blood. Also, transgenic animals may be produced that can express a mutant hemoglobin. Human blood banks must discard human blood after a certain expiration date. This also produces large quantities of hemoglobin.

In addition to extraction from animal sources, the genes encoding subunits of a desired hemoglobin may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., *Proc. Natl. Acad. Sci. USA* 77; 7053–7058 (1980) and Marotta et al., *Journal of Biological Chemistry*, 252; 5040–5053 (1977) respectively. Techniques for expression of both wild-type and mutant alpha and beta globins, and their assembly into a hemoglobin, are set forth in U.S. Pat. No. 5,028,588 and PCT/US90/02654, PCT/US91/09624, and European Patent Application 87116356.9.

Hemoglobin $A_o$ is a heterotetramer composed of two alpha globin subunits ($\alpha_1, \alpha_2$) and two beta globin subunits ($\beta_1, \beta_2$). There is no sequence difference between $\alpha_1$ and $\alpha_2$ or $\beta_1$ and $\beta_2$. In the unoxygenated ("deoxy", or "T" for "tense") state, the subunits form a tetrahedron. The $\alpha_1\beta_1$ and $\alpha_2\beta_2$ interfaces remain relatively fixed during oxygen binding, while there is considerable flux at the $\alpha_1\beta_2$ and $\alpha_2\beta_1$ interfaces. In the oxygenated ("oxy" or "R" or relaxed) state, the intersubunit distances are increased. The subunits are noncovalently associated by Van der Waals forces, hydrogen bonds and, for deoxy Hgb, salt bridges. Hemoglobin is known to dissociate into $\alpha_1\beta_1$ and $\alpha_2\beta_2$ dimers, which are eliminated from the bloodstream by renal filtration. Intravascular retention of hemoglobin has been improved by, e.g., chemical crosslinking of subunits of a single tetramer, or between tetramers.

As taught in U.S. Pat. No. 5,028,588, WO 90/13645, published Nov. 15, 1990, and U.S. patent application Ser. No. 789,179 filed Nov. 8, 1991, it is possible to produce a pseudotetrameric hemoglobin in which two noncovalently associated subunits are replaced by a single pseudodimeric polypeptide with two oxygen binding domains, joined either directly or by a linker of one or more amino acids. This pseudodimeric polypeptide may be expressed from a suitable fused gene. Thus, two alpha globin genes may be fused into a "di-alpha globin" gene, or two beta globin genes into a "di-beta globin" gene, or alpha and beta globin genes into an "alpha beta" globin pseudodimer gene. In any of these forms, hemoglobin is prevented from dissociating into $\alpha 1\beta 1$ and $\alpha 2\beta 2$ dimers, thus increasing the intravascular retention.

Another advantage of fusing two or more globin chains together is that one can selectively mutate one but not both of the chains, as taught in U.S. patent application Ser. No. 789,179 filed Nov. 8, 1991. When hemoglobin is used as a drug delivery vehicle this permits one to provide only one attachment site for a drug of interest so that equimolar amounts of drug and hemoglobin are found in the final product. This also permits creation of an octamer through selective mutation of an amino acid to a cysteine in one of the chains to provide a site for a disulfide linkage.

Another alternative is to have numerous attachment sites on the hemoglobin molecule. This would permit stabilization of higher amounts of the chemical being bound, and would provide the potential for encompassing different release rates of drug bound to one hemoglobin.

Hemoglobin isolated from natural sources has been chemically modified using many techniques in the past. Any of these techniques may be used to prepare hemoglobin. Examples of such modifications are found in U.S. Pat. Nos. 4,412,989, 4,301,144, 4,670,417, 4,321,259, 4,473,563, 4,710,488, 4,650,786, 4,336,248, 4,598,064, 4,600,531 and 4,377,512 among others.

Individual globin chains have been reasserted with modified forms to synthesize a semi-synthetic hemoglobin as well (Luisi et al., *Nature* 320; 555–556 (1986) and Nagai et al., *Nature* 329; 858–860 (1987)). Other modifications such as chemical polymerization of globin chains, glycosylation, pegylation, encapsulation in a liposome or cell membranes are also contemplated.

The hemoglobin produced by expression of recombinant DNA also lends itself to easy modification. By applying the standard techniques of site specific mutagenesis to the globin gene(s), (Kruse et al., *Biotechniques* 6; 338–339 (1988) and Zoller et al., *Methods in Enzymology* 100; 468–500 (1987) are recent examples) one can add, subtract or change any amino acid or combination of amino adds in the resulting globin chain. The modified portions may alter oxygen affinity, for example, or may constitute an attachment site for the drug of interest. This may alter the number and locations where the drug is associated with or binds to the hemoglobin molecule. If the drug of interest is itself a polypeptide, one may add it onto the globin chain to yield a drug-hemoglobin conjugate.

Chemically crosslinked hemoglobins (WO 92/11283, published Jul. 9, 1992; U.S. Pat. No. 4,857,636; U.S. Pat. No. 5,194,590; U.S. Pat. No. 5,084,558), or mutant hemoglobins which genetically fuse the alpha subunits (di-alpha Hgb) or the beta subunits (di-beta Hgb), may increase intravascular retention by inhibiting haptoglobin binding.

Any of the hemoglobins or fragments thereof may be modified to alter the biological activity of the hemoglobin itself. For example, U.S. Pat. Nos. 5,028,588 and 5,173,426 teach use of low oxygen affinity mutants as blood substitutes. Such a modified molecule may also be conjugated to a drug to form a drug-hemoglobin conjugate which is contemplated by the invention.

Preferred hemoglobins are SGE1.1 as well as a mutant (alpha D75C) of the known pseudotetramer SGE1.1 and alpha Lys 16 Cys as described in WO 90/13645, published Nov. 15, 1990, and U.S. patent application Ser. No. 789,179 filed Nov. 8, 1991.

Purification of extracellular hemoglobin can be accomplished using techniques which are well known in the art. A particularly preferred method of purifying recombinant hemoglobin is using the methods described in copending patent application Ser. No. 08/097,273, filed Jul. 23, 1993, entitled Nickel Free Hemoglobin and Methods for Producing Such Hemoglobins.

The extracellular hemoglobin described herein may be used in pharmaceutical compositions as an oxygen carrier, as a blood volume expander or as a drug delivery vehicle. In addition, they may be used in cell cultures to provide oxygen to the cell culture (low affinity hemoglobin) or as an oxygen scavenger in such cell cultures to provide an anaerobic environment (high affinity hemoglobin). High affinity hemoglobins may also be used to deliver oxygen to hypoxic tissues such as tumors (e.g., PCT/US92/04068, published Nov. 26, 1992 and PCT US/US92/04067). Of course the preferred use of extracellular hemoglobins is as a blood substitute instead of transfusions of whole blood from donors.

The present invention provides for such pharmaceutical compositions and formulations for use in delivery of oxygen to tissues, hypoxic tissues, and cell cultures, for stimulation of erythropoiesis, treatment of anemia, and as a drug delivery vehicle for other drugs. The compositions of the invention can be incorporated in conventional solid or liquid pharmaceutical formulations (e.g. tablets, capsules, caplets, injectable or orally administratable solutions) for use in treating mammals in need thereof. The pharmaceutical formulations of the invention comprise a physiologically and/or pharmaceutically effective amount of the extracellular hemoglobin of the present invention as the active ingredients alone or in combination with other active or inert agents. For example, a parenteral therapeutic composition may comprise a sterile isotonic saline solution containing between 0.1 percent and 90 percent weight to volume of hemoglobin. A preferred extracellular hemoglobin solution of tetrameric hemoglobin contains from 1 percent to 10 percent, most preferably about 5 percent hemoglobin in solution weight to volume. The quantity of pharmaceutical provided to the individual is sufficient to provide a blood concentration of between 0.0001 micromolar and 1 millimolar of extracellular hemoglobin. A typical dose of hemoglobin is from 10 mg to 2 gram of extracellular hemoglobin per kilogram of patient body weight. Thus, a typical dose for a human patient will be from a few grams to about 150 grams. It will be appreciated that the unit content of active ingredients contained in an individual dose of each dosage form need not in itself constitute an effective amount since the necessary effective amount can be reached by administration of a plurality of capsules, tablets, injections, etc. or combinations thereof.

Each formulation according to the present invention may additionally comprise inert constituents including pharmaceutically-acceptable carriers, diluents, fillers, salts, and other materials well-known in the art, the selection of which depends upon the dosage form utilized, the condition being treated, the particular purpose to be achieved according to the determination of the ordinarily skilled artisan in the field and the properties of such additives.

The pharmaceutical compositions of the invention may be administered to an individual by any conventional means such as orally, by aerosol, by transdermal adsorption, by adsorption through a mucus membrane or by injection. Parenteral administration is preferred, particularly intravenously or intraarterial.

Administration of extracellular hemoglobin can occur for a period of minutes to hours; however the usual time course is to get oxygen carrying material into a patient as rapidly as possible. Typical infusion rates can be from about 100 ml to 3000 ml/patient/hour, preferably from about 1 ml/kg/hour to about 300 ml/kg/hour, most preferably from about 1 ml/kg/hour to about 25 ml/kg/hour.

Another aspect of the present invention is to novel methods of using extracellular hemoglobin as a treatment for various disorders selected from or resulting from the group consisting of radiation or chemotherapy, erythropoiesis and anemia, coronary angioplasty, and treatment of sickle cell anemia or tissue ischemia. To treat such disorders, extracellular hemoglobin, preferably recombinant hemoglobin can be administered to a patient suffering from such a disorder in an amount that will have the desired therapeutic effect.

ALLEVIATION OF GASTROINTESTINAL EFFECTS ASSOCIATED WITH ADMINISTRATION OF EXTRACELLULAR HEMOGLOBIN

Upon administration of extracellular hemoglobin, it was surprisingly observed that some patients experienced transient mild to moderate gastrointestinal effects. These effects included upper gastrointestinal discomfort including midepigastric discomfort, abdominal pain and/or dyspepsia and/or lower gastrointestinal discomfort including lower abdominal pain, flatulence and/or diarrhea. The gastrointestinal events typically developed 1 to 3 hours post infusion and lasted from one to several hours and waxed and waned over time.

Treatment of these adverse effects can be accomplished using smooth muscle relaxant pharmacological agents. Clinicians are familiar with a number of preparations that can affect smooth muscle tone either directly or indirectly. Such smooth muscle relaxants include β-adrenergic agonists, calcium channel blockers, organic nitrates, anti cholinergic, vasodilators including nitric oxide synthase substrates, $H_1$ and $H_2$ antagonists, cortico steroids, and others. β-adrenergic agonists preferably include terbutaline (Marion Merrell Dow Inc., Kansas City, Mo.). Calcium channel blockers preferably include dihydro pyridine calcium channel blockers, more preferably either nifedipine (Miles Inc., West Haven, Conn., Pratt Pharmaceuticals Division of Pfizer Inc. New York, N.Y.) or nicardipine (Syntex Inc., Palo Alto, Calif.) most preferably nifedipine. Organic nitrates preferably include nitroglycerine (Sanofi Winthrope Pharmaceuticals, New York, N.Y.; Parke-Davis Division of Warner Lambert Co. Morris Plains, N.J.). Anti cholinergic preferably include atropine (Astra Pharmaceutical Products Inc., Westboro, Mass.; Elkins Sinn Inc., Cherry Hill, N.J.). Vasodilators preferably include sodium nitroprusside (Roche Laboratories, a division of Hoffman-La Roche Inc., Nutley, N.J.) and L-arginine (Kabi Pharmacia, Piscataway, N.J.). $H_1$ and $H_2$ antagonists preferably include diphenhydramine (Parke-Davis Division of Warner Lambert Co., Morris Plains, N.J.) and cimetidine (SmithKline Beacham, Philadelphia, Pa.). Cortico steroids preferably include methylprednisolone-acetate (The Upjohn Company, Kalamazoo, Mich.) and hydrocortisone (Merck and Co., Inc., West Point, Pa.). Other smooth muscle relaxants include glucagon (Eli Lilly and Co., Indianapolis, Ind.) and naloxone (Du Pont Multi-Source Products, Du Pont-Merck Pharmaceutical Co., Garden City, N.Y.).

Smooth muscle relaxants can be administered by any acceptable means which are known to clinicians in the field. Admirnistration routes include intravenous, subcutaneous, sub lingual, buccal tablets, oral, aerosol, etc. The various smooth muscle relaxants can be administered alone or in combination with each other. The dosage for a smooth muscle relaxant can be given as a single dose or it can be divided and administered in several independent doses. Sometimes it may be advantageous to administer the dose in larger amounts initially with incrementally smaller doses later to maintain a steady state amount of active ingredient in the patient. Increased initial doses may also be administered when the patients who will receive extracellular hemoglobin are anethetized at the time of commencement of administration of extracellular hemoglobin. Such anethetization often occurs during surgical procedures.

Attending clinicians are familiar with dosage ranges for various smooth muscle relaxants and the dosage amount and regime will often be determined as a result of the severity of the gastrointestinal adverse effects experienced by the patient who has received extracellular hemoglobin. When prophylactic administration of smooth muscle relaxants is used, at least one dose of smooth muscle relaxant is administered prior to the onset of symptoms of adverse effect, preferably prior to commencement of administration of the extracellular hemoglobin. This is often followed by repeated doses of the same smooth muscle relaxant, although such repeated doses are not required nor is it required that the same smooth muscle relaxant be used.

Although many smooth muscle relaxants have detectable ability to lessen the severity and frequency of adverse effects associated with administration of extracellular hemoglobin, certain dosage modes and regimes for some smooth muscle relaxants have more significant effects on lessening adverse effects associated with administration of extracellular hemoglobin, and therefore are preferred embodiments of this invention.

The most preferred smooth muscle relaxants for the present invention are nifedipine and/or terbutaline. Typical dosage amounts and regimes as well as preferred dosage regimes and amounts are as follows:
Prophylactic Treatment Prophylactic treatment for the adverse effects associated with administration of extracellular hemoglobin can be accomplished by prior dosing of the patient with a single smooth muscle relaxant, preferably terbutaline or nifedipine, before commencement of administration of the extracellular hemoglobin. This prior dosing can be followed by repeated subsequent dosing of the same smooth muscle relaxant, preferably terbutaline or nifedipine, after the commencement of administration of the extracellular hemoglobin. Prior dosing can occur at any time from essentially simultaneously with commencement of administration of the extracellular hemoglobin to several hours prior to commencement of administration of the extracellular hemoglobin. Preferably, prior dosing occurs from 10 minutes to 1 hour prior to commencement of administration of the extracellular hemoglobin, most preferably about 30 minutes prior to commencement of administration of the extracellular hemoglobin. Repeated subsequent dosing can occur anywhere from every few minutes to every eight hours after initial administration of the smooth muscle relaxant, preferably from every 30 minutes to every four hours after initial administration of the smooth muscle relaxant, most preferably about every two hours after initial administration of the smooth muscle relaxant. The repeated subsequent dosing can occur for up to a total of 48 hours after commencement of administration of the extracellular hemoglobin, preferably up to a total of 24 hours after commencement of administration of the extracellular hemoglobin, most preferably for about 12 hours after commencement of administration of the extracellular hemoglobin.

The most preferred smooth muscle relaxant for this prophylactic treatment is terbutaline or nifedipine. When any smooth muscle relaxant is used for prophylactic treatment, and particularly when terbutaline or nifedipine is used, there are several dosage modes and regimes that are typically used.

For example, terbutaline can be administered subcutaneously in a prior dose about 30 minutes before commencement of administration of the extracellular hemoglobin in an amount of from 0.05 to 0.50 mg, preferably, 0.10–0.30 mg, most preferably about 0.25 mg. Repeated subsequent doses can be in the same amount and are given about every 2 hours thereafter (i.e., every 2 hours after the initial terbutaline administration), preferably for a total of six terbutaline doses (including the prior dose).

Alternatively, terbutaline can be administered intravenously beginning about 30 minutes before commencement of administration of the extracellular hemoglobin and continuing up to 48 hours after commencement of administration of the extracellular hemoglobin. The infusion rate is typically from 10–25 μg/minute.

Another alternative for administration of terbutaline is for initial administration intravenously, followed by subcutaneous administration, followed by oral administration. Initial intravenous administration can occur as described immediately above and can include the prior dosing and a portion of the repeated subsequent dosing. The subcutaneous administration can occur during the repeated subsequent dosing period followed by oral administration. Oral administration of terbutaline typically occurs in an amount of 5–10 mg p.o. (per oral) four times a day.

When nifedipine is used, it can be administered sublingually in an amount of from 1 to 80 mg, preferably 5 to 40 mg, most preferably about 10 mg. Repeated subsequent doses can be in the same amount and are given about every 2 hours after initial administration of the nifedipine, preferably for a total of six nifedipine doses.

Although terbutaline or nifedipine are the preferred smooth muscle relaxant to use in prophylactic treatment, many other smooth muscle relaxants can be used for prophylactic treatment with dosage amounts adjusted according to the recommended dosages of the manufacturers and the judgment of the attending clinician.

Responsive Regimented Treatment

Responsive regimented treatment for the adverse effects associated with administration of extracellular hemoglobin can be accomplished by repeated subsequent dosing of the a single smooth muscle relaxant, preferably nifedipine, after the commencement of administration of the extracellular hemoglobin or after onset of symptoms of adverse effects from administration of extracellular hemoglobin. Repeated subsequent dosing can occur anywhere from every few minutes to every eight hours after onset of clinical symptoms of adverse gastrointestinal adverse effects, preferably from every 30 minutes to every four hours after onset of clinical symptoms of adverse gastrointestinal adverse effects, most preferably about every two hours after onset of clinical symptoms of adverse gastrointestinal adverse effects. The repeated subsequent dosing can occur for up to a total of 48 hours after onset of clinical symptoms of adverse gastrointestinal adverse effects, preferably up to a total of 24 hours after onset of clinical symptoms of adverse gastrointestinal adverse effects, most preferably for about 12 hours after onset of clinical symptoms of adverse gastrointestinal adverse effects.

The most preferred smooth muscle relaxant for this responsive regimented treatment is nifedipine. When any smooth muscle relaxant is used for responsive regimented treatment, and particularly when nifedipine is used, there are several dosage modes and regimes that are typically used. For example, nifedipine can be administered sublingually in an amount of from 1 to 80 mg, preferably 5 to 40 mg, most preferably about 10 mg. Repeated subsequent doses can be in the same amount and are given about every 2 hours after commencement of administration of the extracellular hemoglobin, preferably for a total of six nifedipine doses.

Although nifedipine is the preferred smooth muscle relaxant to use in responsive regimented treatment, many other smooth muscle relaxants can be used for such treatment with dosage amounts adjusted according to the recommended dosages of the manufacturers and the judgment of the attending clinician. Although the responsive regimented treatment may be effective with the use of some smooth muscle relaxants, in general, his method of treatment is not as effective in alleviating adverse effects associated with administration of extracellular hemoglobin.

Responsive Intermittent Treatment

Responsive intermittent treatment for the adverse effects associated with administration of extracellular hemoglobin can be accomplished by dosing of a single smooth muscle relaxant, preferably nifedipine, as discretionary determined by the attending clinician taking into account such factors as the severity of the adverse gastrointestinal effects experienced by the patient. This responsive intermittent treatment can also preferably be implemented as an adjunct to a prophylactic treatment method as described above, preferably a prophylactic treatment method utilizing terbutaline for prior dosing or using terbutaline for both prior dosing and subsequent repeated dosing. Whether the responsive intermittent treatment is used in conjunction with a prophylactic treatment or not, it is utilized if the patient experiences symptoms of adverse effects after commencement of administration of extracellular hemoglobin.

For example, in some cases where prophylactic treatment using terbutaline is implemented, the patient may still experience some gastrointestinal discomfort after administration of extracellular hemoglobin. This experience of adverse effects after initial prophylactic treatment, known as "breakthrough" can be treated acutely by this responsive intermittent treatment method. The preferred smooth muscle relaxant for use in responsive intermittent treatment is nifedipine. Typically, from 1–80 mg of nifedipine can be administered subligually or orally, preferably 5 to 40 mg, most preferably about 10 mg. Dosing can be repeated as necessary.

Although nifedipine is the preferred smooth muscle relaxant to use in responsive intermittent treatment, many other smooth muscle relaxants can be used for such treatment with dosage amounts adjusted according to the recommended dosages of the manufacturers and the judgment of the attending clinician.

The methods of the present invention are useful to alleviate adverse effects associated with the administration of extracellular hemoglobin, particularly adverse effects relating to gastrointestinal discomfort.

and/or lower gastrointestinal discomfort including lower abdominal pain, flatulence and/or diarrhea. Abdominal examinations during these events were benign. The effects lasted from one to several hours and waxed and waned over time.

TABLE 1

| Dose Level (g/kg) | Total # of Subjects | Dysphagia | | | Upper GI Discomfort[b] | | | Nausea | | | Vomiting | | | Lower GI Discomfort[c] | | | Diarrhea | | |
|---|---|---|---|---|---|---|---|---|---|---|---|---|---|---|---|---|---|---|---|
| | | mild | mod. | sev. | mild | mod. | sev. | mild | mod. | sev. | mild | mod. | sev. | mild | mod. | sev. | mild | mod. | sev. |
| 0.015 | 4 | 0 | 0 | 0 | 0 | 0 | 0 | 0 | 0 | 0 | 0 | 0 | 0 | 0 | 0 | 0 | 0 | 0 | 0 |
| 0.075 | 4 | 0 | 0 | 0 | 0 | 0 | 0 | 2 | 0 | 0 | 0 | 0 | 0 | 1 | 0 | 0 | 0 | 0 | 0 |
| 0.110 | 4 | 0 | 0 | 0 | 0 | 0 | 0 | 1 | 1 | 0 | 0 | 1 | 0 | 0 | 0 | 0 | 0 | 0 | 0 |
| 0.05–0.09 | 4 | 0 | 0 | 0 | 0 | 0 | 0 | 0 | 0 | 0 | 0 | 0 | 0 | 0 | 0 | 0 | 0 | 0 | 0 |
| 0.150 | 38 | 9 | 0 | 0 | 18 | 12 | 0 | 10 | 6 | 0 | 7 | 6 | 0 | 9 | 3 | 0 | 5 | 0 | 0 |
| 0.180 | 5 | 1 | 0 | 0 | 2 | 2 | 0 | 3 | 0 | 0 | 1 | 1 | 0 | 1 | 0 | 0 | 1 | 0 | 0 |
| Total | 59 | 10 | 0 | 0 | 20 | 14 | 0 | 16 | 7 | 0 | 8 | 8 | 0 | 11 | 3 | 0 | 6 | 0 | 0 |

[a]Number of subjects who reported the gastrointestinal symptom.
[b]Upper GI discomfort = epigastric discomfort, abdominal pain and/or dyspepsia.
[c]Lower GI discomfort = lower abdominal pain, flatulence and/or diarrhea.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references cited herein are hereby incorporated by reference for their relevant teachings.

EXAMPLES

The following examples are provided by way of describing specific embodiments of the present invention without intending to limit the scope of the invention in any way.

Example 1

Administration of Extracellular Hemoglobin to a Patient in Need of a Red Blood Cell Transfusion Prior to receiving rHb1.1, subjects were fasted from 0 to 11 hours. Some subjects were hydrated with D-5 half normal saline at up to 500 cc/hr (cc=ml) beginning 2 hours prior to infusion with Hb. A five percent weight to volume (5% w:v) solution of hemoglobin (rHb1.1) in a pharmaceutical composition was administered by intravenous infusion (taking care to protect from exposure to light) to patients at a rate of 3.75 ml/kg/hr for up to two hours so that a total dose of rHb1.1 of up to about 25 grams was administered. Table 1 shows the gastrointestinal effects of rHb1.1 at doses up to 0.18 g/kg. As can be seen, several symptoms indicated unusual smooth muscular contraction.

Most of the subjects dosed with ≧0.15 g/kg of rHb1.1 developed transient mild to moderate gastrointestinal adverse effects. In 16 patients dosed with ≧0.11 g/kg, rHb1.1, only 2 reported these symptoms. The gastrointestinal events typically developed 1 to 3 hours post infusion and consisted of upper gastrointestinal discomfort including mid-epigastric discomfort, abdominal pain and/or dyspepsia Example 2

Prophylactic Treatment of Gastrointestinal Adverse Effects Associated with Administration of Extracellular Hemoglobin Utilizing Terbutaline To decrease the incidence and/or severity of gastrointestinal effects associated with administration of extracellular hemoglobin, terbutaline was administered to the patient prophylactically. Prior to receiving rHb1.1, subjects were fasted about 10 hours. Beginning at 2 hours prior to rHb1.1 infusion, subjects were hydrated with D-5 half normal saline at 500 cc/hr, which was decreased to 250 cc/hr at the start of rHb1.1 infusion. Hydration continued for 4 hours post-infusion. rHb1.1 was administered at doses ranging from 0.15 g/kg to 0.32 g/kg, resulting in total doses from about 12 to 25 grams per subject. One-half hour prior to administration of rHb1.1, 0.25 mg of terbutaline sulfate was administered to the patient subcutaneously. Successive doses of terbutaline in an amount of 0.25 mg each were administered subcutaneously every two hours after initial administration of terbutaline. A total of six doses of terbutaline were administered.

The results are shown in Table 2. The number of patients who experienced symptoms of different severity levels when given doses of rHb1.1 between 12 and 14 g without prophylactic treatment with terbutaline is compared to number of patients experiencing the same levels of severity when given doses of rHb1.1 of up to 25 grams with terbutaline prophylaxis. The severity was reduced with prophylaxis, even when up to two times as much rHb1.1 was administered.

TABLE 2

| | None | Mild | Moderate | Severe |
|---|---|---|---|---|
| Before prophylaxis with terbutaline (n = 37) | 7 (19%) | 15 (41%) | 15 (41%) | 0 |

TABLE 2-continued

|  | None | Mild | Moderate | Severe |
|---|---|---|---|---|
| (~12–14 g) After prophylaxis with terbutaline (n = 14) (~12–25 g) | 3 (21%) | 8 (57%) | 3 (21%) | 0 |

Example 3

Regimented Treatment of Gastrointestinal Adverse Effects Associated with Administration of Extracellular Hemoglobin Utilizing Nifedipine To decrease the incidence and/or severity of gastrointestinal effects associated with administration of extracellular hemoglobin, nifedipine was administered to the patient prophylactically. Prior to receiving rHb1.1, subjects were fasted about 10 hours. Beginning at 2 hours prior to rHb1.1 infusion, subjects were hydrated with D-5 half normal saline at 500 cc/hr, which was decreased to 250 cc/hr at the start of rHb1.1 infusion. Hydration continued for 4 hours post-infusion. rHb1.1 was administered at 0.15 g/kg, resulting in total doses from about 8.9 to 12.3 g per subject. One-half hour prior to administration of rHb1.1, 10 mg of nifedipine was administered to the patient sublingually. Successive doses of nifedipine in an amount of 10 mg each were administered sublingually at 2, 4, 6, 9 and sometimes 12 hours after initial administration of the nifedipine. A total of five to six doses of nifedipine were administered.

One third of the subjects experienced no symptoms. Symptoms were generally classified as mild, but the response was not as stable as the response to terbutaline.

Example 4

Acute Responsive Intermittent Treatment of Gastrointestinal Adverse Effects Associated with Administration of Extracellular Hemoglobin To decrease the severity of gastrointestinal effects associated with administration of extracellular hemoglobin, various drugs were administered to the patient intermittently after onset of symptoms as determined by a physician upon the onset or recurrence of gastrointestinal discomfort. One subject, for example, received 15.77 grams rHb1.1. At 2.5 hours post infusion, the subject received naloxone 2 mg IV. At 3 hours post infusion, the subject received glucagon 1 mg intravenously (IV). The discomfort decreased somewhat but intensified a short time later, at which time the subject received nitroglycerine 1/150 grams sublingually. The subject received 10 mg nifedipine sublingually at 3.5 hours postinfusion and a second dose of glucagon 1 mg IV at 4 hours. Glucagon 0.5 mg IV was administered again at 5.5 and 9 hours post infusion.

Except for the naloxone dose, each treatment resulted in a decrease in epigastric discomfort. However, all improvements were judged to be more transient and less satisfactory than obtained with other treatments described.

Example 5

Acute Responsive Intermittent Treatment of Gastrointestinal Adverse Effects Associated with Administration of Extracellular Hemoglobin Utilizing Nifedipine To decrease the incidence and/or severity of gastrointestinal effects associated with administration of extracellular hemoglobin, nifedipine was administered to the patient intermittently as determined by a physician upon the onset or recurrence of gastrointestinal discomfort. Prior to receiving rHb1.1, subjects were fasted about 10 hours. Beginning at 2 hours prior to rHb1.1 infusion, subjects were hydrated with D-5 half normal saline at 500 cc/hr, which was decreased to 250 cc/hr at the start of rHb1.1 infusion. Hydration continued for 4 hours post-infusion. rHb1.1 was administered at 0.15 g/kg, resulting in total dosage from about 11.3 to 13.1 grams per subject. One-half hour prior to administration of rHb1.1, 10 mg of nifedipine was administered to the patient sublingually. Subsequent to infusion of rHb1.1, 10 mg of nifedipine was administered to the subject sublingually only upon onset or recurrence of symptoms and as determined by the physician until gastrointestinal discomfort was relieved. For example, one subject received nifedipine at 2.75 hours, 8 hours, and 11.5 hours post infusion.

All subjects experienced symptoms which progressed to moderate levels of discomfort by 8 hours post infusion.

Example 6

Combined Treatment of Gastrointestinal Adverse Effects Associated with Administration of Extracellular Hemoglobin Utilizing Terbutaline and Nifedipine To decrease the incidence and/or severity of gastrointestinal effects associated with administration of extracellular hemoglobin, terbutaline sulfate was administered to the patient prophylactically followed by intermittent dosing with nifedipine. Prior to receiving rHb1.1, subjects were fasted about 10 hours. Beginning at 2 hours prior to rHb1.1 infusion, subjects were hydrated with D-5 half normal saline at 500 cc/hr, which was decreased to 250 cc/hr at the start of rHb1.1 infusion. Hydration continued for 4 hours post-infusion. rHb1.1 was administered at 0.25 g/kg or at 0.32 g/kg. One-half hour prior to administration of rHb1.1, 0.25 mg of terbutaline was administered to the patient subcutaneously, followed by 5 additional 0.25 mg doses every 2 hours after initial administration of the terbutaline. Doses of nifedipine in an amount of 10 mg each were administered sublingually by the physician only upon onset or reappearance of discomfort and as determined by the physician. For example, one subject received a dose at 2 hours post infusion, another dose 15 minutes later, and a third dose at 3.25 hours. Another subject received only one dose at 3 hours.

The clinical observation was that while use of two drugs was not always indicated, (a) this regiment worked better than either drug alone, and (b) nifedipine worked better and resolved discomfort faster when given as needed in conjunction with terbutaline prophylaxis than when given alone.

I claim:

1. A method of treating various disorders selected from or resulting from the group consisting of radiation or anemia or tissue ischemia comprising administering to those in need thereof a therapeutically effective amount of extracellular, recombinant hemoglobin.

2. The method according to claim 1 wherein the extracellular, recombinant hemoglobin comprises mutant hemoglobin.

3. The method according to claim 2 wherein the mutant hemoglobin comprises pseudotetrameric hemoglobin.

4. The method according to claim 3 wherein the pseudotetrameric hemoglobin comprises rHb1.1.

5. A method of treating anemia comprising administering to those in need thereof a therapeutically effective amount of extracellular, recombinant hemoglobin.

6. The method of claim 5 wherein the extracellular, recombinant hemoglobin comprises mutant hemoglobin.

7. The method of claim 6 wherein the mutant hemoglobin comprises pseudotetrameric hemoglobin.

8. The method of claim 7 wherein the pseudotetrameric hemoglobin comprises rHb1.1.

9. A method of treating tissue ischemia comprising administering to those in need thereof a therapeutically effective amount of extracellular, recombinant hemoglobin.

10. The method of claim 9 wherein the extracellular, recombinant hemoglobin comprises mutant hemoglobin.

11. The method of claim 10 wherein the mutant hemoglobin comprises pseudotetrameric hemoglobin.

12. The method of claim 11 wherein the pseudotetrameric hemoglobin comprises rHb1.1.

13. A method of treating tissue ischemia comprising administering to those in need thereof a therapeutically effective amount of polymerized hemoglobin.

14. The method according to claim 13 wherein the polymerized hemoglobin comprises polymerized recombinant hemoglobin.

* * * * *